US012752022B2

(12) United States Patent
Osada et al.

(10) Patent No.: US 12,752,022 B2
(45) Date of Patent: Oct. 6, 2026

(54) SINGLE-POLYMER PARTICLES, ACTIVE MOLECULAR COMPLEX, METHOD FOR PRODUCING SINGLE-POLYMER PARTICLES, METHOD FOR MEASURING TUMOR SIZE, METHOD FOR MEASURING FINE STRUCTURE WITHIN TUMOR, METHOD FOR IMAGING BIOLOGICAL TISSUE, DRUG DELIVERY SYSTEM, AND CONTRAST AGENT KIT

(71) Applicant: NATIONAL INSTITUTES FOR QUANTUM SCIENCE AND TECHNOLOGY, Chiba (JP)

(72) Inventors: Kensuke Osada, Chiba (JP); Kazuaki Rikiyama, Chiba (JP); Akira Sumiyoshi, Chiba (JP); Ichio Aoki, Chiba (JP); Kanjiro Miyata, Tokyo (JP); Mitsuru Naito, Tokyo (JP); Yusuke Watanuki, Tokyo (JP)

(73) Assignee: NATIONAL INSTITUTES FOR QUANTUM SCIENCE AND TECHNOLOGY, Chiba (JP)

( * ) Notice: Subject to any disclaimer, the term of this patent is extended or adjusted under 35 U.S.C. 154(b) by 0 days.

(21) Appl. No.: 18/855,346

(22) PCT Filed: Mar. 24, 2023

(86) PCT No.: PCT/JP2023/011719

§ 371 (c)(1),
(2) Date: Dec. 9, 2024

(87) PCT Pub. No.: WO2023/199723

PCT Pub. Date: Oct. 19, 2023

(65) Prior Publication Data

US 2025/0325714 A1 Oct. 23, 2025

(30) Foreign Application Priority Data

Apr. 14, 2022 (JP) ................................ 2022-067148

(51) Int. Cl.
*A61K 49/12* (2006.01)
*G01R 33/28* (2006.01)

(52) U.S. Cl.
CPC .......... *A61K 49/126* (2013.01); *G01R 33/282* (2013.01)

(58) Field of Classification Search
CPC .... A61B 5/4848; A61B 5/4842; A61K 47/60; A61K 51/0402; A61K 47/6811; A61K 39/0011
See application file for complete search history.

(56) References Cited

U.S. PATENT DOCUMENTS

2002/0187199 A1* 12/2002 Ranger .................... B01J 13/02 424/501
2008/0241073 A1 10/2008 Yokoyama et al.
(Continued)

FOREIGN PATENT DOCUMENTS

CN 101306196 A * 11/2008
JP 2021-020872 2/2021
(Continued)

OTHER PUBLICATIONS

International Search Report for PCT/JP2023/011719 and its English translation, dated May 30, 2023.
(Continued)

*Primary Examiner* — Gerald Johnson
(74) *Attorney, Agent, or Firm* — Casimir Jones, S.C.; Robert A. Goetz

(57) ABSTRACT

An embodiment of the present invention has an object of providing single-macromolecule particles each having a more accurately controlled hydrodynamic diameter, an
(Continued)

active molecular complex, a method for producing the single-macromolecule particles, and a method for imaging biological tissue. In order to attain the object, provided are single-macromolecule particles characterized by each being formed of a single macromolecule and by having a molecular weight distribution $M_w/M_n$ of not more than 1.5. This makes it possible to obtain particles each having an accurately controlled hydrodynamic diameter. The single macromolecule is preferably a structure consisting of a single hydrophilic macromolecule A or a structure in which one or more side chains are bonded to a main chain, the main chain being the single hydrophilic macromolecule A, each of the one or more side chains being a hydrophilic macromolecule B.

20 Claims, 6 Drawing Sheets

(56) References Cited

U.S. PATENT DOCUMENTS

2013/0071482 A1 3/2013 Bae et al.
2018/0140680 A1 5/2018 Kataoka et al.
2020/0360545 A1* 11/2020 Hearn .................. A61K 9/0019
2021/0346472 A1 11/2021 Kataoka et al.
2022/0242973 A1* 8/2022 Fiedler .................... A61P 35/00
2023/0157963 A1* 5/2023 Moaseri ................. A61K 47/38
424/439

FOREIGN PATENT DOCUMENTS

WO 2006/003731 1/2006
WO 2016/021407 2/2016
WO 2016/178431 11/2016
WO 2018/207864 11/2018
WO WO-2021201488 A1 * 10/2021 ................ A61P 7/02
WO WO-2021202659 A1 * 10/2021 ............... B60C 1/00

OTHER PUBLICATIONS

Written Opinion for PCT/JP2023/011719 and its English translation, dated May 30, 2023.
Horacio Cabral, et al., Chem.Rev. 2018, 118, 6844-6892.
Sumiyo Watanabe et al. "In vivo rendezvous of small nucleic acid drugs with charge-matched block catiomers to target cancers" Nature Communications, (2019) 10, 1894, 29 pages.
Mitsuru Naito et al. "Size-tunable PEG-grafted copolymers as a polymeric nanoruler for passive targeting muscle tissues", Journal of Controlled Release 347 (2022) 607-614.

* cited by examiner

SINGLE-POLYMER PARTICLES, ACTIVE MOLECULAR COMPLEX, METHOD FOR PRODUCING SINGLE-POLYMER PARTICLES, METHOD FOR MEASURING TUMOR SIZE, METHOD FOR MEASURING FINE STRUCTURE WITHIN TUMOR, METHOD FOR IMAGING BIOLOGICAL TISSUE, DRUG DELIVERY SYSTEM, AND CONTRAST AGENT KIT

TECHNICAL FIELD

The present invention relates to particles each having an accurately controlled hydrodynamic diameter. More specifically, the present invention relates to single-macromolecule particles each consisting of a single macromolecule, an active molecular complex, a method for producing the single-macromolecule particles, a method for measuring a size of a tumor, a method for measuring a fine structure within a tumor, a method for imaging biological tissue, a drug delivery system, and a contrast agent kit.

BACKGROUND ART

A low-molecular drug such as an anticancer drug, a contrast agent, or an antisense therapeutic agent has a molecular size of not more than 5 nm in itself and is therefore quickly discharged from the kidney in a case where the low-molecular drug is administered into blood. This makes it difficult to deliver the low-molecular drug to a target site. Further, it is known that the small molecular size of the low-molecular drug causes the low-molecular drug to undergo transudation from blood vessels, and this results in damage to the surrounding tissue.

In such cases, by bonding a small molecule to a macromolecule to form an aggregate or bonding a small molecule to a lipid to form an aggregate to thereby make it appear that the molecular weight has increased, it is possible to prevent the discharge from the kidney and the transudation from the blood vessels and to promote delivery of the low-molecular drug to the target site. Such a technique of controlling the molecular weight of a drug to thereby control the behavior of the drug in a body is called passive targeting and is studied as one of the fields of drug delivery system (DDS) technology.

For example, Patent Literature 1 discloses a nuclear magnetic resonance contrast agent in which macromolecule micelles containing a hydrophilic polymer chain segment are used. In this technology, the molecular weight of the hydrophilic, low-molecular contrast agent is controlled with use of the polymer micelles, so that the contrast agent is delivered effectively to a target site.

Non-patent Literature 1 indicates that micelles consisting of a block copolymer have great potential to serve as a nanomedicine capable of controlling the distribution and function of a biologically active agent such as a drug, a protein, or a nucleic acid and thus effectively overcoming a biological barrier.

CITATION LIST

Patent Literature

[Patent Literature 1]
International Publication No. WO2006/003731

Non-Patent Literature

[Non-patent Literature 1]
Horacio Cabral, et al., Chem. Rev. 2018, 118, 6844-6892

SUMMARY OF INVENTION

Technical Problem

However, in the technology of Patent Literature 1, polymer micelles are aggregates each formed of a large number of macromolecules. This makes it difficult to accurately control the molecular weights of the particles and causes unevenness in particle size. This makes it difficult to accurately control the behavior of the contrast agent in a body. Also in the technology of Non-Patent Literature 1 it is similarly difficult to accurately control the size of each particle.

Further, each of the polymer micelles used in the above technologies is an aggregate formed of a large number of macromolecules. As such, the polymer micelles generally have a relatively large hydrodynamic diameter of approximately 30 nm to 80 nm, and it is technically difficult to form polymer micelles that are particles having a small hydrodynamic diameter.

It is an object of an embodiment of the present invention to provide single-polymer particles each having a more accurately controlled hydrodynamic diameter, an active molecular complex, a method for producing the single-macromolecule particles, a method for measuring a size of a tumor, a method for measuring a fine structure within a tumor, a method for imaging biological tissue, a drug delivery system, and a contrast agent kit.

Solution to Problem

The inventor of the present invention conducted diligent study on the above object, and consequently attained a knowledge that, by using single-macromolecule particles having a molecular weight distribution of not more than 1.5, it is possible to obtain particles each having an accurately controlled hydrodynamic diameter. Thus, the inventor of the present invention completed the present invention.

Specifically, an embodiment of the present invention provides <1> through <16> below.

<1> Single-macromolecule particles, each formed of a single macromolecule, the single macromolecule having a molecular weight distribution $M_w/M_n$ of not more than 1.5.

This makes it possible to obtain particles each having an accurately controlled hydrodynamic diameter.

<2> The single-macromolecule particles as set forth in claim 1, wherein the single macromolecule is a structure consisting of a single hydrophilic macromolecule A or a structure in which one or more side chains are bonded to a main chain, the main chain consisting of the single hydrophilic macromolecule A, each of the one or more side chains being a hydrophilic macromolecule B.

This makes it possible to obtain particles each having a more accurately controlled hydrodynamic diameter.

<3> The single-macromolecule particles as set forth in claim 1 or 2, wherein the hydrophilic macromolecule A is a polypeptide, a polysaccharide, a vinyl-based macromolecule, a polyether-based macromolecule, a polyester-based macromolecule, or a polyoxazoline.

This makes it possible to easily control the molecular weight of the single macromolecule. As a result, it is possible to control hydrodynamic diameters of the single-macromolecule particles.

<4> The single-macromolecule particles as set forth in any one of claims 1 to 3, wherein the hydrophilic macromolecule B is polyalkylene glycol, polyvinyl alcohol, polyvinyl pyrrolidone, polyhydroxyethyl methacrylate, poly(2-methoxyethyl acrylate), a polyoxazoline, carboxymethyl cellulose, methyl cellulose, hydroxyethyl cellulose, or a carboxy vinyl polymer.

This makes it possible to easily control the molecular weight of the single macromolecule. As a result, it is possible to control hydrodynamic diameters of the single-macromolecule particles.

<5> The single-macromolecule particles as set forth in any one of claims 1 to 4, wherein the number of the one or more side chains each of which is the hydrophilic macromolecule B and which are bonded to the hydrophilic macromolecule A is not less than 1 and not more than 100.

This makes it possible to obtain particles each having a more accurately controlled hydrodynamic diameter.

<6> The single-macromolecule particles as set forth in any one of claims 1 to 5, wherein the single macromolecule has a molecular weight of not less than 10 kDa and not more than 1500 k Da.

This makes it possible to obtain particles each having a more accurately controlled hydrodynamic diameter.

<7> The single-macromolecule particles as set forth in any one of claims 1 to 6, wherein:

the hydrophilic macromolecule A is polyaspartic acid; and the hydrophilic macromolecule B is polyethylene glycol.

This makes it possible to obtain particles each having a more accurately controlled hydrodynamic diameter.

<8> An active molecular complex, including:

the single-macromolecule particles recited in any one of claims 1 to 7; and an active molecule bonded to the single-macromolecule particles.

This makes it possible to control the behavior of the active molecular complex in a living body.

<9> The active molecular complex as set forth in claim 8, wherein the active molecule is an antibody drug, an antisense therapeutic agent, a low-molecular drug, a radiopharmaceutical, a contrast agent, or a chromophore.

This makes it possible to obtain a complex of (i) an antibody drug, an antisense therapeutic agent, a low-molecular drug, a radiopharmaceutical, a contrast agent, or a chromophore and (ii) the single-macromolecule particles, the behavior of which complex in a living body is controlled.

<10> A method for producing single-macromolecule particles, the method including:

(i) synthesizing a hydrophilic macromolecule A by a ring-opening polymerization reaction using an $\alpha$-amino acid-N-carboxy anhydride as a raw material, the hydrophilic macromolecule A being linear; and (ii) bonding a hydrophilic macromolecule B to a reactive site of the hydrophilic macromolecule A.

This makes it possible to obtain particles each having an accurately controlled hydrodynamic diameter.

<11> A method for measuring a size of a tumor, the method including measuring the size of the tumor with use of single-macromolecule particles recited in any one of claims 1 to 7 or an active molecular complex recited in claim 8 or 9.

This makes it possible to measure a size of a tumor.

<12> A method for measuring a fine structure within a tumor, the method including measuring the fine structure within the tumor with use of single-macromolecule particles recited in any one of claims 1 to 7 or an active molecular complex recited in claim 8 or 9.

This makes it possible to measure a fine structure within a tumor.

<13> A method for imaging biological tissue with use of single-macromolecule particles recited in any one of claims 1 to 7 or an active molecular complex recited in claim 8 or 9.

This makes it possible to more accurately image biological tissue.

<14> The method as set forth in claim 13, wherein the biological tissue is a tumor.

This makes it possible to more accurately image a tumor.

<15> A drug delivery system, transporting single-macromolecule particles recited in any one of claims 1 to 7 or an active molecular complex recited in claim 8 or 9 to an intended location in a living body.

This makes it possible to transport single-macromolecule particles or the like to an intended location in a living body.

<16> A contrast agent kit, including a plurality of active molecular complexes having respective different sizes, each of the plurality of active molecular complexes being recited in claim 8 or 9.

This makes it possible to more accurately know a fine structure of biological tissue.

Advantageous Effects of Invention

According to an embodiment of the present invention, it is possible to provide single-polymer particles each having a more controlled hydrodynamic diameter, an active molecular complex, a method for producing the single-macromolecule particles, a method for measuring a size of a tumor, a method for measuring a fine structure within a tumor, a method for imaging biological tissue, a drug delivery system, and a contrast agent kit.

DESCRIPTION OF EMBODIMENTS

Figure 1:
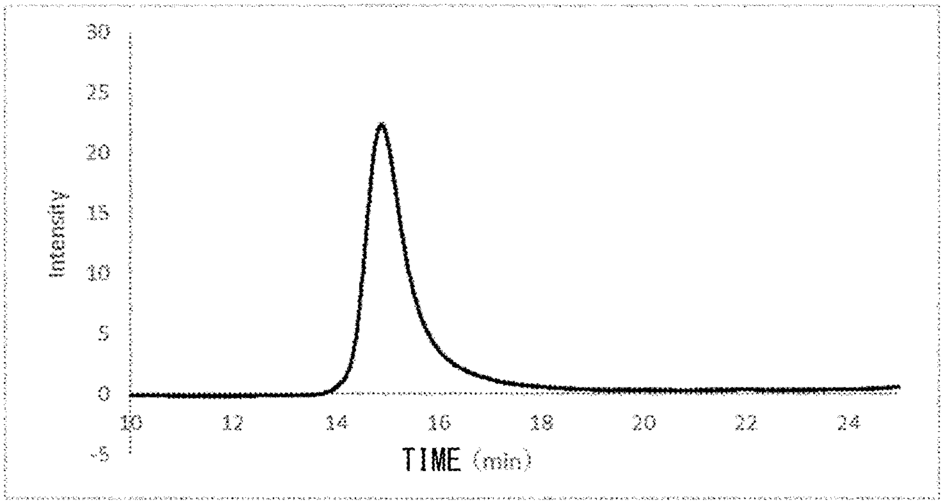
FIG. 1 indicates a result of analysis of a molecular weight distribution of synthesized PBLA by GPC.

The following description will discuss in detail an embodiment of single-macromolecule particles, an active molecular complex, a method for producing the single-macromolecule particles, and a method for imaging biological tissue in accordance with the present invention.

Note that single-macromolecule particles, an active molecular complex, a method for producing the single-macromolecule particles, and a method for imaging biological tissue described in the embodiment are merely examples for describing the present invention, and the present embodiment is not limited to such examples.

Definitions

As used herein, a "macromolecule" is a molecule of high relative molecular mass, the structure of which essentially includes the multiple repetition of units derived, actually or conceptually, from molecules of low relative molecular mass. The "macromolecule" is also referred to as a "polymer molecule". Such macromolecules are roughly categorized into biomacromolecules and synthetic macromolecules. Specific examples of a biomacromolecule include a polypeptide formed of amino acid units, a polysaccharide formed of monosaccharide units, and a polynucleotide formed of nucleic acid units. Specific examples of a synthetic macromolecule include: a polyester-based macromolecule formed of units of a polyvalent carboxylic acid and a polyalcohol; a vinyl-based macromolecule which is a macromolecule obtained by polymerization of vinyl groups (CH2═CH—); an ether-based macromolecule which is a macromolecule having an ether linkage (—C—O—C—) in a main chain; and a polyamide formed of units of a polyvalent carboxylic acid and a polyvalent amine.

As used herein, a "single macromolecule" means a single macromolecule which is formed by covalent bonding and which is not a complex of a plurality of molecules obtained by a hydrogen bond, a hydrophobic bond, a van der Waals force, or the like. As used herein, "single-macromolecule particles" means a state in which individual single macromolecules are dispersed in an aqueous solvent without having secondary association in the molecules in the aqueous solvent, and exhibit properties of a particle. A single-macromolecule particle in accordance with an embodiment of the present invention does not encompass a complex formed of a plurality of macromolecules, such as a micelle. Further, a "single-macromolecule particle" means a particle formed of a single macromolecule unless otherwise specified. Note that a molecular weight distribution $M_w/M_n$ of macromolecules refers to a molecular weight distribution in a set of single-macromolecule particles which are obtained by an identical production method or the like and are substantially identical to each other.

As used herein, "biocompatibility" means a property of having affinity for biological tissue and organs and not causing a foreign body reaction, a rejection reaction, or the like. The present invention is intended to be used mainly in a living body, and preferably, a macromolecule having biocompatibility is used as the above-described macromolecule.

As used herein, a "molecular weight" is a molecular weight determined by TOF-MS, a molecular weight calculated and determined from the protons of a terminal group by NMR, or a molecular weight calculated from both thereof.

As used herein, a "number average molecular weight ($M_n$)" is a molecular weight calculated from an average (arithmetic mean) of molecular weights of macromolecules included in a set of synthesized macromolecules. The number average molecular weight is determined by gel permeation chromatography (GPC).

As used herein, a "weight average molecular weight ($M_w$)" is an average molecular weight calculated on the basis of a weight fraction, and is an average which is calculated using, as an index, not the number of polymer chains but a "weight (a molecular weight×the number of polymer chains)". The weight average molecular weight is determined by GPC.

As used herein, a "molecular weight distribution" means a degree of distribution of molecular weights and polymerization degrees of macromolecules, i.e., a degree of variation in molecular weight and polymerization degree. The molecular weight distribution is determined by GPC. The molecular weight distribution is indicated by a value of a ratio ($M_w/M_n$) of the weight average molecular weight $M_w$ to the number average molecular weight $M_n$. In a case where the molecular weight distribution is 1.0 to 1.5, it is determined that the macromolecules are substantially monodispersed. The molecular weight distribution is determined by GPC.

As used herein, a "hydrodynamic diameter" means a size of a particle estimated from a speed of movement of the particle. A hydrodynamic diameter d can be determined by measuring diffusion time by fluorescence correlation spectroscopy and calculating the hydrodynamic diameter d using the Einstein-Stokes relational formula (equation (1)). In the present specification, a "hydrodynamic diameter" is used synonymously with a "size of a particle".

$$d=kT/3\pi\eta_0 D \quad \text{(Equation (1))}$$

(k: Boltzmann constant, T: absolute temperature, η: solvent viscosity, translational diffusion coefficient: D)

[Single-Macromolecule Particles]

Single-macromolecule particles in accordance with an embodiment of the present invention are characterized by each being formed of a single macromolecule and by having a molecular weight distribution $M_w/M_n$ of not more than 1.5. This makes it possible to obtain particles each having an accurately controlled hydrodynamic diameter.

A living body has a mechanism of controlling, in accordance with sizes of particles taken into the living body, the behavior of the particles in the living body (e.g., a mechanism of allowing particles of sizes not greater than a certain size to pass through and not allowing particles of sizes greater than the certain size to pass through). Use of the single-macromolecule particles in accordance with an embodiment of the present invention makes it possible to accurately control the behavior of the particles within the body in accordance with a purpose. By employing the single-macromolecule particles in accordance with an embodiment of the present invention, for example, it is possible to use the single-macromolecule particles as a contrast agent. By adjusting the size of the single-macromolecule particles in accordance with an embodiment of the present invention, it is possible to put the single-macromolecule particles to uses such as use for the purpose of preventing the single macromolecule from leaking out of a blood vessel, use for the purpose of causing renal excretion in order to discharge the single macromolecule from the living body early, use for the purpose of avoiding renal excretion in order to retain the single macromolecule within the living body, use as single-macromolecule particles capable of being delivered to deep levels of tissue, use for the purpose of imaging biological tissue, use for the purpose of measuring a size of tissue or visualizing a fine structure of the tissue, use, for therapeutic purposes, of single-macromolecule particles or an active molecular complex to which a drug having an appropriate hydrodynamic diameter or size is bonded, and use for the purpose of transporting the active molecular complex to an intended location in the living body.

Specific examples of the above-described examples of use include the following.

By bonding, to the particles, Gd ions which are used in a contrast agent, it is possible to efficiently deliver the particles only to a target site to thereby avoid failure caused by transudation from blood vessels and avoid toxicity to other parts such as the brain.

It is possible to prepare, while avoiding renal excretion, particles of a size (a few nm to tens of nm) deliverable to deep levels of an inflamed site or cancers tissue to which it is impossible to deliver conventional particles of a size of micelles or the like (tens to hundreds of nm).

By visualizing a fine structure of tissue with use of particles of an accurately controlled size and using, in treatment in accordance with a result of the visualization, particles (active molecular complex) to which a drug of an appropriate size is bonded, it is possible to carry out the treatment effectively.

The single-macromolecule particles in accordance with an embodiment of the present invention have a molecular weight distribution of not more than 1.5. An upper limit value of the molecular weight distribution is preferably not more than 1.4, more preferably not more than 1.3, and even more preferably not more than 1.2. In a case where the molecular weight distribution of the single-macromolecule particles is within the above range, it is possible to obtain particles each having a more accurately controlled hydrodynamic diameter.

The hydrodynamic diameter of each of the single-macromolecule particles in accordance with an embodiment of the present invention varies depending on the application of the single-macromolecule particles, but is, for example, 1 nm to 100 nm. The hydrodynamic diameter of each of the single-macromolecule particles can be controlled by controlling the molecular weight of the single macromolecule. The molecular weight of a single macromolecule can be controlled by controlling the respective molecular weights of a hydrophilic macromolecule A and a hydrophilic macromolecule B and/or the number of bonds of the hydrophilic macromolecule B, as described later.

Further, in the above-described examples of application of the single-macromolecule particles, the single-macromolecule particles in accordance with an embodiment of the present invention each have a hydrodynamic diameter of preferably not less than 0.5 nm and more preferably not less than 1 nm in a case where, for example, the single-macromolecule particles are used as a contrast agent.

In a case where the single-macromolecule particles in accordance with an embodiment of the present invention are used for the purpose of preventing leakage from blood vessels, the hydrodynamic diameter is preferably not less than 2 nm and more preferably not less than 3 nm.

In a case where the single-macromolecule particles in accordance with an embodiment of the present invention are used for the purpose of causing renal excretion in order to discharge the single-macromolecule particles from the living body early, the hydrodynamic diameter is preferably less than 5 nm.

In a case where the single-macromolecule particles in accordance with an embodiment of the present invention are used for the purpose of avoiding renal excretion in order to retain the single-macromolecule particles within the living body, the hydrodynamic diameter is preferably not less than 5 nm and more preferably not less than 6 nm.

In a case where the single-macromolecule particles in accordance with an embodiment of the present invention are used as single-macromolecule particles capable of being delivered to deep levels of tissue, the hydrodynamic diameter is preferably as small as possible, preferably not more than 100 nm and more preferably not more than 30 nm.

The single-macromolecule particles can be formed into a single-macromolecule particle composition containing a plurality of single-macromolecule particles. The single-macromolecule particle composition ordinarily contains a set of single-macromolecule particles which are obtained by an identical production method or the like, more preferably a set of single-macromolecule particles which are substantially identical to each other. A molecular weight distribution $M_w/M_n$ in the single-macromolecule particle composition represents a molecular weight distribution of the single-macromolecule particles in the single-macromolecule particle composition. A preferable range of each constituent element in the single-macromolecule particle composition is similar to a preferable range in the single-macromolecule particles.

The following description will first discuss components constituting the single-macromolecule particles in detail.

(Single Macromolecule)

The single-macromolecule particles in accordance with an embodiment of the present invention are each formed of a single macromolecule. The single macromolecule is preferably a macromolecule formed mainly of hydrophilic units, and more preferably a macromolecule formed solely of hydrophilic units. It is preferable that the single macromolecule have no hydrophobic units. It is also preferable that the single macromolecule have the property of being present in the form of single macromolecular chains in an aqueous solvent without inter-molecular secondary association.

The single macromolecule is not particularly limited, but is a structure consisting solely of a single hydrophilic macromolecule A or a structure in which one or more side chains, each of which is a hydrophilic macromolecule B, are bonded to the single hydrophilic macromolecule A. From the perspective of accurately setting a molecular size within a wider range, it is preferable that the single macromolecule be a structure in which one or more side chains, each of which is the hydrophilic macromolecule B, are bonded to the single hydrophilic macromolecule A.

In a case where the single macromolecule is a structure in which one or more side chains, each of which is the hydrophilic macromolecule B, are bonded to a main chain consisting of the single hydrophilic macromolecule A, it is preferable that hydrophilic macromolecule B have a specific molecular weight. The single macromolecule has a structure of, for example, a graft copolymer, which is a polymer including: a single macromolecule as a main chain; and macromolecules of another type branched from the single macromolecule.

The single-macromolecule particles each have a molecular weight which is set as appropriate in accordance with the purpose of use of the single-macromolecule particles and is preferably 1 kDa to 2000 kDa. A lower limit value of the molecular weight is more preferably not less than 2 kDa, and even more preferably not less than 5 kDa. An upper limit value of the molecular weight is preferably not more than 1750 kDa, and more preferably not more than 1500 kDa. Hydrodynamic diameters of the single-macromolecule particles can be controlled by controlling the molecular weight of the single macromolecule.

Specific examples of a method for controlling the molecular weight of the single macromolecule include (i) synthesis through graft copolymerization, (ii) obtaining a macromolecule having a narrow molecular weight distribution by living polymerization or ring-opening polymerization, or (iii) obtaining a fraction having an appropriate molecular weight by fractionation after production.

<Hydrophilic Macromolecule A>

The hydrophilic macromolecule A forms a main chain of a single macromolecule. The hydrophilic macromolecule A, for example, has a linear or branched structure. The hydrophilic macromolecule A preferably has a linear structure. The hydrophilic macromolecule A is not particularly limited, but is preferably a macromolecule mainly composed of a linear structure, and more preferably a macromolecule composed solely of a linear structure. The hydrophilic macromolecule A is not particularly limited to specific ones provided that the hydrophilic macromolecule A is a hydrophilic macromolecule. Preferably, the hydrophilic macromolecule A is a biocompatible macromolecule. Examples of such a biocompatible macromolecule include a polypeptide, a polysaccharide, a vinyl-based macromolecule, a polyether-based macromolecule, a polyester-based macromolecule, a polyoxazoline, and a polynucleotide. Among these examples, from the perspective of ease in molecular weight control, the biocompatible macromolecule is preferably a polypeptide or a polyamino acid, and more preferably polyaspartic acid, polyglutamic acid, or polylysine.

A molecular weight distribution of the hydrophilic macromolecule A is not particularly limited, but is preferably not more than 1.5. An upper limit value of the molecular weight distribution is more preferably not more than 1.4, even more preferably not more than 1.3, and still even more preferably not more than 1.2. In a case where the molecular weight distribution of the hydrophilic macromolecule A is within the above range, it is possible to better control the molecular weight distribution of the single-macromolecule particles. The molecular weight distribution of the single-macromolecule particles is greatly affected by the molecular weight distribution of the hydrophilic macromolecule A, which is a main chain of the single macromolecule. As such, it is important to control the molecular weight distribution of the hydrophilic macromolecule A.

A molecular weight of the hydrophilic macromolecule A is not particularly limited, but is, for example, 1 kDa to 100 kDa. A lower limit value of the molecular weight is preferably not less than 1 kDa, and more preferably not less than 2 kDa. An upper limit value of the molecular weight is preferably not more than 80 kDa, and not more than 50 kDa.

From the perspective of ease in molecular weight control, the hydrophilic macromolecule A is particularly preferably a polypeptide which has been synthesized through a ring-opening polymerization reaction with use of an α-amino acid-N-carboxy anhydride as a raw material.

<Hydrophilic Macromolecule B>

The hydrophilic macromolecule B is bonded, as a side chain, to the main chain consisting of the hydrophilic macromolecule A. A molecular weight distribution of the hydrophilic macromolecule B is preferably not more than 1.5, more preferably not more than 1.4, even more preferably not more than 1.3, still even more preferably not more than 1.2, and particularly preferably not more than 1.1. The hydrophilic macromolecule B is bonded to any of the reactive sites which are present in the hydrophilic macromolecule A.

The hydrophilic macromolecule B is not particularly limited to specific ones provided that the hydrophilic macromolecule B is a hydrophilic macromolecule. Preferably, the hydrophilic macromolecule B is a hydrophilic biocompatible macromolecule. Examples of the hydrophilic macromolecule B include polyalkylene glycol (having, for example, 2 to 4 carbon atoms), polyvinyl alcohol (PVA), polyvinyl pyrrolidone, polyhydroxyethyl methacrylate (PHEMA), poly(2-methoxyethyl acrylate) (PMEA), a polyoxazoline, carboxymethyl cellulose, methyl cellulose, hydroxyethyl cellulose, and a carboxy vinyl polymer. Among these examples, from the perspective of ease in molecular weight control, the hydrophilic biocompatible macromolecule is preferably polyethylene glycol (PEG). Specific examples of the polyethylene glycol include PEG500, PEG2000, PEG5000, PEG10000, PEG20000, PEG40000, and PEG80000.

A molecular weight of the hydrophilic macromolecule B is not particularly limited, but is, for example, 0.01 kDa to 1000 kDa. A lower limit value of the molecular weight is preferably not less than 0.02 kDa, more preferably not less than 0.05 kDa, and even more preferably not less than 0.1 kDa. An upper limit value of the molecular weight is preferably not more than 500 kDa, more preferably not more than 200 kDa, and even more preferably not more than 100 kDa.

The number of hydrophilic macromolecules B bonded to a single hydrophilic macromolecule A is not particularly limited, but is, for example, 0 to 200. A lower limit value of the number of hydrophilic macromolecules B bonded to a single hydrophilic macromolecule A is preferably not less than 0, more preferably not less than 1, and even more preferably not less than 3. An upper limit value of the number of hydrophilic macromolecules B bonded to a single hydrophilic macromolecule A is preferably not more than 150, more preferably not more than 100, and even more preferably not more than 50.

[Active Molecular Complex]

An active molecular complex in accordance with an embodiment of the present invention is a complex obtained by bonding an active molecule to the above-described single-macromolecule particles. This makes it possible to control the behavior of the active molecular complex in a living body. Bonding of the active molecule is, for example, covalent bonding, ionic bonding, or the like. The bonding also encompasses coordination of a metal ion, which is used as a contrast agent or the like, to a chelate-forming functional group in a single macromolecule. The chelate-forming functional group is a functional group which has an element (N, O, P, S, or the like) having a lone electron pair and donates the electrons of the lone electron pair to a metal ion to form a robust coordinate bond.

(Active Molecule)

The active molecule is not particularly limited, and may be a general active molecule which is used in the field of medicines, diagnostic agents, or the like. Preferably, the active molecule is an antibody drug, a low-molecular drug, an antisense therapeutic agent, a radiopharmaceutical, a contrast agent, or a chromophore.

The antibody drug is not particularly limited, and may be one which is obtained by bonding a drug such as a low-molecular drug to an antibody that specifically binds to a disease-associated molecule and which is targeted to, for example, cancers or autoimmune diseases.

The antibody used in the antibody drug is not particularly limited, and may be any of a polyclonal antibody, a monoclonal antibody, and a fragment thereof (for example, Fab, F(ab)2, etc.). Further, the class and the subclass of an immunoglobulin is not particularly limited. The antibody may be one that is selected from an antibody library by a phage display method or the like, or may be a conventionally-known antibody.

The low-molecular drug is not particularly limited, but is primarily a synthesized chemical substance having a molecular weight of not more than 500. Examples of the low-molecular drug include an anticancer drug.

The antisense therapeutic agent is not particularly limited, and examples of the antisense therapeutic agent include a polynucleotide or an oligonucleotide formed of DNA, RNA, or a derivative thereof. The polynucleotide is single stranded or double stranded. The polynucleotide may be a sequence encoding a protein, or may be a sequence that does not encode a protein.

Examples of the radiopharmaceutical include technetium ($^{99m}$Tc), thallium ($^{201}$Tl), gallium ($^{67}$Ga), indium ($^{111}$In), and fluorine ($^{18}$F). In a case where the radiopharmaceutical is used as the active molecule, the active molecular complex can be subjected to imaging by positron emission tomography (PET) or single-photon emission computed tomography (SPECT).

Examples of the contrast agent include gadolinium, manganese, iron, and iodine. In a case where the contrast agent is used as the active molecule, the active molecular complex can be subjected to imaging by magnetic resonance imaging (MRI).

Examples of the chromophore include fluorescein isothiocyanate (FITC).

[Method for Producing Single-Macromolecule Particles]

A method in accordance with an embodiment of the present invention for producing single-macromolecule particles is not particularly limited, but examples of the method include: synthesis by polycondensation between an amino acid and a carboxylic acid; and solid-phase synthesis of peptides. Among syntheses by polycondensation between an amino acid and a carboxylic acid, a ring-opening polymerization reaction using an α-amino acid-N-carboxy anhydride as a raw material is preferable.

The ring-opening polymerization reaction using an α-amino acid-N-carboxy anhydride as a raw material is characterized by including the following steps.

(i) A step of synthesizing a linear hydrophilic macromolecule A by a ring-opening polymerization reaction using an α-amino acid-N-carboxy anhydride as a raw material.

(ii) A step of bonding a hydrophilic macromolecule B to a reactive site of the hydrophilic macromolecule A.

The method in accordance with an embodiment of the present invention for producing single-macromolecule particles makes it possible to easily produce particles each of which has a more accurately controlled hydrodynamic diameter and which are low in molecular weight distribution. Further, by more strictly controlling each phase of the production method, it is possible to adjust the hydrodynamic diameter of the produced particles in nanometers and produce single-macromolecule particles having a wide range of molecular weights.

The step (i) is a step of synthesizing a linear hydrophilic macromolecule A by a ring-opening polymerization reaction using an α-amino acid-N-carboxy anhydride (also referred to as "α-amino acid-NCA") as a raw material. As the raw material, an α-amino acid-N-carboxy anhydride or a derivative thereof is used. From the perspective of suppressing a side reaction, in a case where the amino acid has a highly-reactive functional group in a side chain thereof, it is preferable that the functional group be modified with a protecting group. Specific examples of the highly-reactive functional group include a carboxyl group. Examples of a raw material having such a protecting group include a benzyl ester of an α-amino acid-N-carboxy anhydride.

The step (ii) is a step of bonding a hydrophilic macromolecule B, which is a side chain, to a reactive site of a main chain, which is formed of the hydrophilic macromolecule A. The reactive site is not particularly limited, but is preferably a highly-reactive functional group. Specific examples of the highly-reactive functional group include a carboxyl group.

[Method for Imaging Biological Tissue]

A method in accordance with an embodiment of the present invention for imaging biological tissue is characterized by using the above-described single-macromolecule particles or the active molecular complex in accordance with an embodiment of the present invention. As such, by capturing an image of biological tissue, it is possible to obtain more detailed information of a tissue structure.

Further, by capturing an image of biological tissue with use of single-macromolecule particles or the like having an accurately controlled size (i.e., an accurately controlled hydrodynamic diameter), it is possible to visualize a fine structure of the tissue. Further, it is at the same time possible to obtain information pertaining to a hydrodynamic diameter or a size that allows permeation to deep levels of the tissue. It is also possible to carry out more effective treatment by using, in accordance with that result, a drug of an appropriate hydrodynamic diameter or size or using, in the treatment in accordance with the result, single-macromolecule particles or an active molecular complex to which the drug is bonded.

[Method for Measuring Size of Tumor]

A method in accordance with an embodiment of the present invention for measuring a size of a tumor uses a plurality of single-macromolecule particles having respective different sizes (i.e., hydrodynamic diameters) or a plurality of active molecular complexes having respective different sizes (i.e., hydrodynamic diameters). By capturing an image of a tumor with use of the plurality of single-macromolecule particles or the like controlled to have respective different two or more hydrodynamic diameters, it is possible to visualize a fine structure of tissue of the tumor and obtaining information pertaining to a hydrodynamic diameter or a size that allows permeation to deep levels of the tissue. It is also possible to carry out more effective treatment of the tumor by using, in accordance with that result, a drug of an appropriate hydrodynamic diameter or size or using, in the treatment in accordance with the result, single-macromolecule particles or an active molecular complex to which the drug is bonded.

[Method for Measuring Fine Structure within Tumor]

A method in accordance with an embodiment of the present invention for measuring a fine structure within a tumor is characterized by measuring the fine structure within the tumor with use of single-macromolecule particles or an active molecular complex. In the method for measuring the fine structure, it is possible to not only measure a size of the entire tumor but also measure a fine structure within the tumor on the basis of information pertaining to whether or not the single macromolecule can pass through. It is also possible to carry out more effective treatment by selecting, in accordance with that result, a drug of an appropriate hydrodynamic diameter or size.

[Drug Delivery System]

A drug delivery system in accordance with an embodiment of the present invention is characterized by transporting single-macromolecule particles or an active molecular complex to an intended location in a living body. As described above, a living body has a mechanism of controlling, in accordance with sizes of particles taken into the living body, the behavior of the particles in the living body (e.g., a mechanism of allowing particles of sizes not greater than a certain size to pass through and not allowing particles of sizes greater than the certain size to pass through). The drug delivery system in accordance with an embodiment of the present invention makes it possible to accurately control, in accordance with a purpose, the behavior of the single-macromolecule particles in accordance with an embodiment of the present invention in the body by controlling sizes of the particles.

[Contrast Agent Kit]

A contrast agent kit in accordance with an embodiment of the present invention is characterized by including active molecular complexes having respective different two or more sizes (i.e., hydrodynamic diameters). By using a plurality of single-macromolecule particles or the like controlled to have respective different two or more hydrodynamic diameters, it is possible to obtain information pertaining to a hydrodynamic diameter or a size that allows permeation to deep levels of the tissue. It is also possible to carry out more effective treatment by selecting, in accordance with that result, a drug of an appropriate hydrodynamic diameter or size.

EXAMPLES

The following description will discuss Examples of the present invention. The present invention is not limited to these Examples, and the Examples may be altered in various ways within the technical ideas of the present invention.

(Raw Materials)

Table 1 indicates raw materials which were used in Examples below. Among the raw materials, n-butylamine, N,N-dimethylformamide, and dichloromethane used were those which had gone through distillation with use of calcium hydride.

TABLE 1

| Compound name (product name) | Manufacturer/distributor |
|---|---|
| n-butylamine | Manufactured by FUJIFILM Wako Pure Chemical Corporation |
| N,N-dimethylformamide | Manufactured by FUJIFILM Wako Pure Chemical Corporation |
| Dichloromethane | Manufactured by FUJIFILM Wako Pure Chemical Corporation |
| β-benzyl-L-aspartic acid N-carboxylic acid anhydride | Manufactured by Chuo Kaseihin Co., Inc. |
| Methoxy-PEG2000 (MEPA-20H) | Manufactured by NOF CORPORATION |
| Methoxy-PEG5000 (MEPA-50H) | Manufactured by NOF CORPORATION |
| Methoxy-PEG12000 (MEPA-12T) | Manufactured by NOF CORPORATION |
| Methoxy-PEG20000 (MEPA-20T) | Manufactured by NOF CORPORATION |
| 1-ethyl-3-(3-dimethylaminopropyl)carbodiimide hydrochloride | Manufactured by FUJIFILM Wako Pure Chemical Corporation |

TABLE 1-continued

| Compound name (product name) | Manufacturer/distributor |
|---|---|
| N-hydroxysuccinimide | Manufactured by FUJIFILM Wako Pure Chemical Corporation |
| Diethyl ether | Manufactured by FUJIFILM Wako Pure Chemical Corporation |
| Acetonitrile | Manufactured by FUJIFILM Wako Pure Chemical Corporation |
| Sodium hydroxide | Manufactured by FUJIFILM Wako Pure Chemical Corporation |
| Azido-PEG4-amine | manufactured by Tokyo Chemical Industry Co., Ltd. |
| Sodium hydrogen carbonate | Manufactured by FUJIFILM Wako Pure Chemical Corporation |
| Sulfo-Cy5-DBCO | Manufactured by Lumiprobe Corporation |
| D-PBS(—) | Manufactured by FUJIFILM Wako Pure Chemical Corporation |

1. Experiment 1: Synthesis of Main Chain Consisting of Polyaspartic Acid (1) Synthesis of Polyaspartic Acid (PAsp)

A main chain consisting of polyaspartic acid (PAsp) was synthesized by the following procedure.

1000 mg of β-benzyl-L-aspartic acid N-carboxylic acid anhydride (NCA-BLA) was weighed in a round-bottomed flask and dissolved in 10 mL of N,N-dimethylformamide (DMF). In another round-bottomed flask, 360 μL of a solution obtained by diluting n-butylamine 100-fold with dichloromethane and 10 mL of DMF were added and mixed. The entire NCA-BLA solution was added to the n-butylamine solution, and a resultant solution was stirred for 5 days at a temperature maintained at 35° C. All of the above reactions were carried out in an argon atmosphere, and all of the organic solvents employed were used after going through distillation. After the reaction, the reaction solution was dropped into 400 mL of diethyl ether, and polyaspartic acid-β-benzyl (PBLA) was precipitated. Then, the precipitate was collected by suction filtration and was dried under reduced pressure. The PBLA thus obtained was subjected to analysis of a molecular weight distribution by GPC and measurement of a molecular weight and a polymerization degree by NMR. The measurement results are shown in Table 2.

TABLE 2

| | Molecular weight (kDa) | Molecular weight distribution ($M_w/M_n$) | Polymerization degree |
|---|---|---|---|
| PBLA | 13.5 | 1.170 | 117 |

Subsequently, 100 mg of PBLA was suspended in 4 mL of acetonitrile, and then 4.9 mL of a 0.5 M aqueous sodium hydroxide solution was added. The resultant solution was caused to react overnight at room temperature to cause deprotection of a benzyl group from PBLA. Then, the reaction solution was supplied to a dialysis membrane (molecular weight cutoff: 6,000 to 8,000), and dialysis was carried out twice with use of pure water as an external solution, twice with use of 0.01 M hydrochloric acid as an external solution, and twice with use of pure water as an external solution again (each for not less than 2 hours). The resultant product was subjected to freeze-drying to obtain polyaspartic acid (PAsp).

(2) Introduction of Azido Group into Carboxylic Acid Groups (Side Chains) of Polyaspartic Acid In order to measure a hydrodynamic diameter by fluorescence correlation spectroscopy, an azido group was introduced, by the following procedure, into carboxylic acid groups which were side chains of PAsp.

To 10 mg of polyaspartic acid measured, 2.5 mL of 50 mM sodium hydrogen carbonate was added, and the polyaspartic acid was dissolved in the 50 mM sodium hydrogen carbonate. 289.6 μL of azido-PEG4-amine having a concentration adjusted to 30 μM with use of DMF was added, and 27 mg of 1-ethyl-3-(3-dimethylaminopropyl) carbodiimide hydrochloride (EDC) was added. The resultant mixture was stirred at room temperature for 3 hours. Then, the reaction solution was supplied to a dialysis membrane (molecular weight cutoff: 6,000 to 8,000), and dialysis was carried out twice with use of pure water as an external solution, three times with use of a 0.01 M aqueous sodium hydroxide solution as an external solution, three times with use of 0.01 M hydrochloric acid as an external solution, and twice with use of pure water as an external solution again (each for not less than 2 hours). The resultant product was subjected to freeze-drying to obtain polyaspartic acid (PAsp ($N_3$)) having azido groups introduced to some of the side chains thereof. An introduction ratio of the azido groups in the obtained PAsp($N_3$) was calculated by NMR. Results of the experiment are shown in Table 3.

TABLE 3

| | Introduction ratio of azido groups (%) | Number of azido groups introduced |
|---|---|---|
| Pasp($N_3$) | 11% | 13 |

2. Experiment 2: Synthesis of Single Macromolecule (1) Introduction of Side Chains to PAsp($N_3$) (Side Chains: PEG2000, PEG5000, and PEG12000)

To a main chain consisting of PAsp($N_3$), any one of PEG2000, PEG5000, and PEG12000 was introduced as a side chain by the following procedure to produce a single macromolecule.

2 mg each of PAsp($N_3$) synthesized in Experiment 1 was weighed and dissolved in 1 mL of DMF. In other sample bottles, methoxy-PEG2000, methoxy-PEG5000, and methoxy-PEG12000 were respectively dissolved in DMF at a concentration of 50 mg/mL, and the resultant solutions were respectively added to the PAsp($N_3$) solutions such that an amount of each of methoxy-PEG2000, methoxy-PEG5000, and methoxy-PEG12000 was 2 equivalents with respect to a carboxy group of PAsp($N_3$). Subsequently, EDC was added in an amount of 5 equivalents with respect to the carboxy group of PAsp($N_3$), and the resultant mixture was stirred for 3 hours. The number of PEG chains introduced to PAsp($N_3$) was calculated by measuring, by GPC, an amount of decrease in peak area of each PEG as compared with an initial value.

Results of the GPC are shown in Table 4. Note that PAsp having PEG grafted as a side chain thereof will hereinafter be referred to as PAsp-g-PEGXX (XX is a molecular weight of PEG which was a side chain).

(2) Introduction of Side Chain to PAsp($N_3$) (Side Chain: PEG20000)

To a main chain consisting of PAsp($N_3$), PEG20000 was introduced as a side chain by the following procedure to produce a single macromolecule.

2 mg each of PAsp($N_3$) was weighed and dissolved in 1 mL of DMF. In another sample bottle, PEG20000 was dissolved in DMF at a concentration of 50 mg/mL, and the resultant solution was respectively added to the PAsp($N_3$) solution such that an amount of PEG20000 was 2 equivalents with respect to a carboxy group of PAsp($N_3$). Subsequently, NHS was dissolved in DMF at a concentration of 25 mg/mL, and the resultant solution was added such that an amount of NHS was 1.2 equivalents with respect to the carboxy group of PAsp($N_3$). Then, EDC was added in an amount of 0.95 equivalents with respect to the carboxy group of PAsp($N_3$), and the resultant mixture was stirred for 3 hours. The number of PEG chains introduced to PAsp($N_3$) was calculated by measuring, by GPC, an amount of decrease in peak area of each PEG as compared with an initial value. The measurement results are shown in Table 4.

TABLE 4

| | Number of side chains introduced |
|---|---|
| PAsp-g-PEG2000 | 80 |
| PAsp-g-PEG5000 | 74 |
| PAsp-g-PEG12000 | 60 |
| PAsp-g-PEG20000 | 66 |

After each PAsp-g-PEG was synthesized, fractionation was carried out by GPC in order to remove unreacted PEG. The reaction solution was supplied to a dialysis membrane (molecular weight cutoff: 6,000 to 8,000), and dialysis was carried out three times with use of 10 mM phosphate buffer as an external solution and three times with use of pure water as an external solution. The resultant product was subjected to freeze-drying to obtain PAsp-g-PEG in powder form.

(3) Introduction of Fluorescent Dye into Each PAsp-g-PEG (to be Used Later in Measurement of Size (and Measurement of Behavior in Body) by Fluorescence Correlation Spectroscopy, not Essential)

In order to measure a size by fluorescence correlation spectroscopy, a fluorescent dye (sulfo-Cy5-DBCO) was introduced into each PAsp-g-PEG by the following procedure.

PAsp-g-PEG was dissolved in pure water at a concentration of 25 mg/mL. Sulfo-Cy5-DBCO was dissolved in DMSO at a concentration of 25 mg/ml and added such that an amount of sulfo-Cy5-DBCO was 1 equivalent with respect to an azido group of a side chain of PAsp-g-PEG. The mixed solution was subjected to freezing at −20° C. and melting in a refrigerator at +4° C., repeatedly for a total of three times. Then, in order to remove unreacted sulfo-Cy5-DBCO, purification was carried out with a PD-10 column, and the resultant product was collected by freeze-drying.

3. Experiment 3: Measurement of Physical Properties of PAsp-g-PEG (1) Evaluation of Hydrodynamic Diameter of Each PAsp-g-PEG Each PAsp-g-PEG in which sulfo-Cy5 was labeled was diluted with D-PBS(−) so as to have a concentration of 2 nM, and was subjected to measurement of diffusion time by fluorescence correlation spectroscopy. A hydrodynamic diameter was calculated using the Einstein-Stokes relational formula. At this time, Cy5 was used as a standard substance in calculation of a diffusion coefficient. Results of the measurement by fluorescence correlation spectroscopy are shown in Table 5.

(2) Molecular Weight of Each PAsp-g-PEG

A molecular weight of the entire single macromolecule was calculate by adding, to the molecular weight of the main chain measured by the NMR measurement, a value based on molecular weight of PEG measured by TOF-MS and the number of side chains introduced. A value thus obtained was regarded as a molecular weight of an entire single macromolecule. Results are shown in Table 5.

(3) Measurement of Molecular Weight Distribution of Each PAsp-g-PEG

Figure 2:
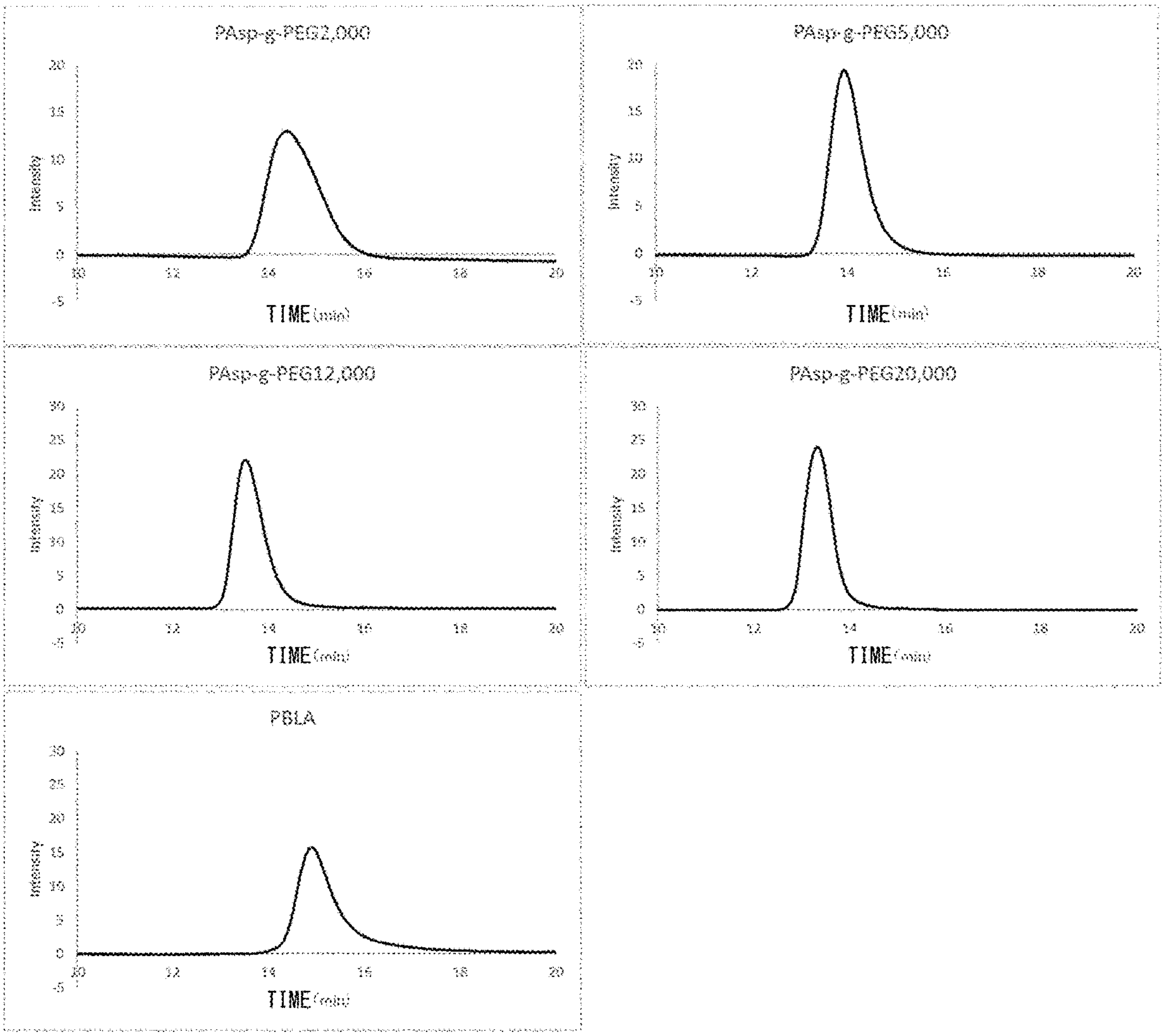
FIG. 2 indicates a result of analysis of synthesized PAsp-g-PEG2000, PAsp-g-PEG5000, PAsp-g-PEG12000, and PAsp-g-PEG20000 by GPC.

A molecular weight distribution ($M_w/M_n$) of each PAsp-g-PEG was measured by gel permeation chromatography (GPC). Results of the experiment are shown in Table 5 and FIG. 2.

TABLE 5

| | Molecular weight (kDa) | Molecular weight distribution ($M_w/M_n$) | Average hydrodynamic diameter (nm) |
|---|---|---|---|
| PAsp-g -$PEG_{2,000}$ | 176.9 | 1.181 | 11.0 ± 0.3 |
| PAsp-g -$PEG_{5,000}$ | 384.2 | 1.190 | 15.0 ± 0.3 |
| PAsp-g -$PEG_{12,000}$ | 735.4 | 1.268 | 21.8 ± 0.9 |
| PAsp-g -$PEG_{20,000}$ | 1339.7 | 1.270 | 31.7 ± 1.9 |

Figure 3:
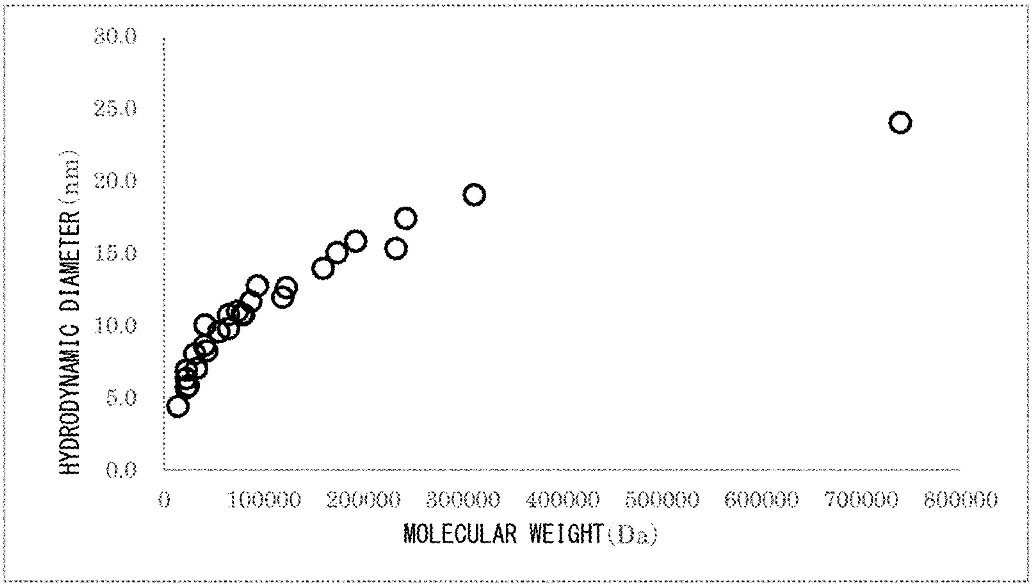
FIG. 3 indicates a result of synthesis of single-macromolecule particles having a controlled hydrodynamic diameter.

As indicated in FIG. 3, it was found that by adjusting a molecular weight, it was possible to obtain a series of macromolecules each having a hydrodynamic diameter controlled with precision in nanometers within a range of 4 nm to 25 nm.

Figure 4:
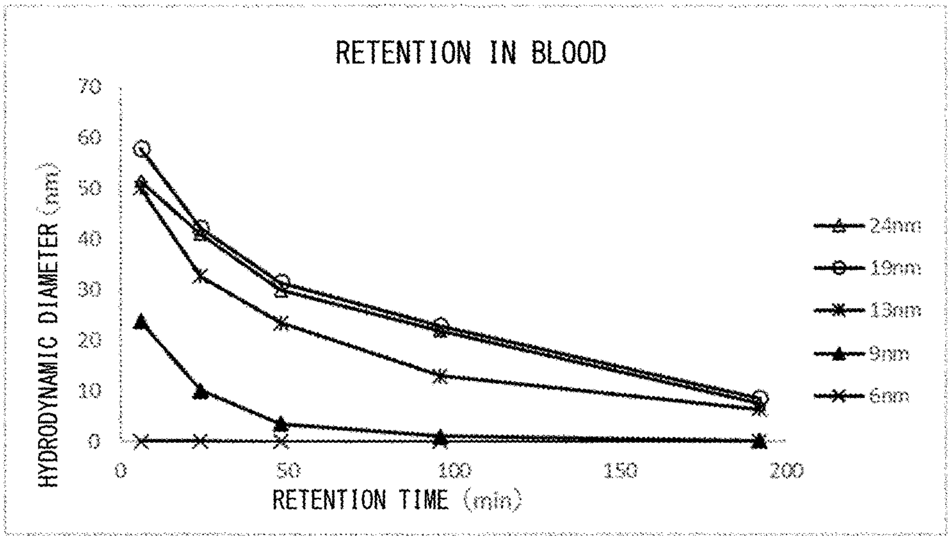
FIG. 4 indicates a result of a test of retention in blood of single-macromolecule particles.

As a result of the test of retention in blood, it was confirmed that, as indicated in FIG. 4, macromolecules having a hydrodynamic diameter of 6 nm disappeared early from the blood, and macromolecules having a hydrodynamic diameter of not less than 19 nm exhibited long retention in blood, namely, a half-life in blood of 4 days.

Figure 5:
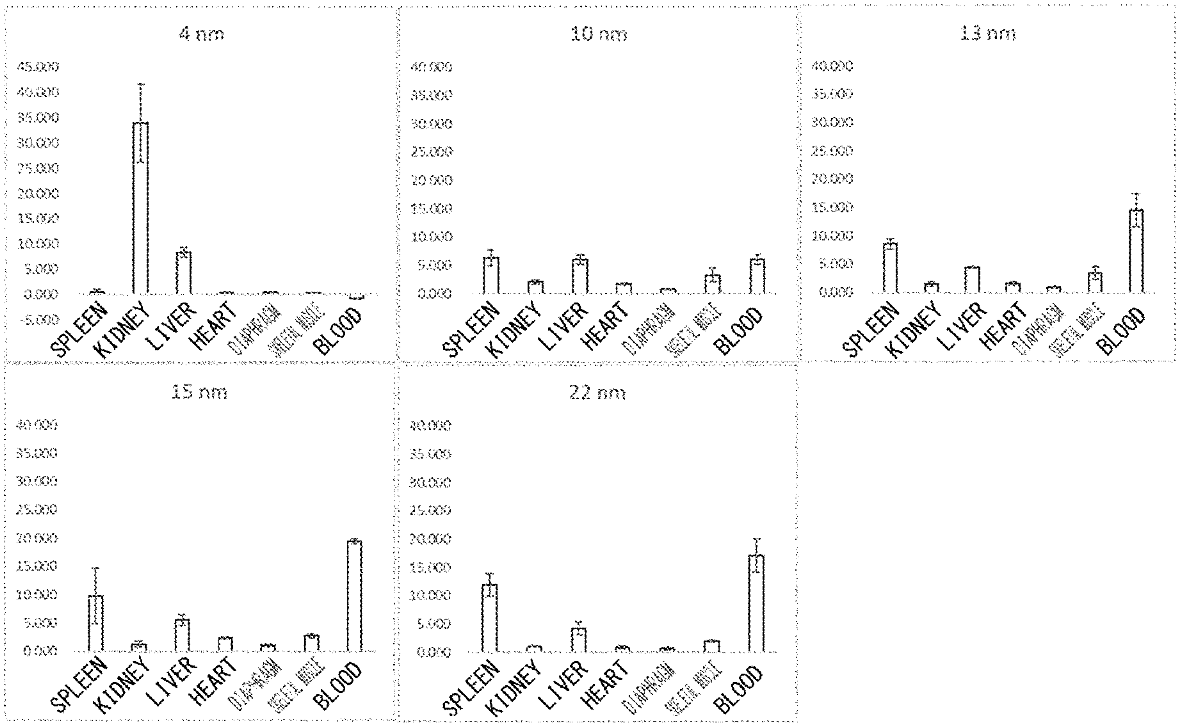
FIG. 5 indicates a hydrodynamic diameter of single-macromolecule particles and a behavior of the single-macromolecule particles in a body after intravenous administration.

5. Experiment 5: Evaluation of Behavior of Single-Macromolecule Particles in Body of Muscular Dystrophy Model Mouse Fluorescently-labelled single-macromolecule particles were intravenously administered to a muscular dystrophy model mouse, and a distribution in the body was evaluated 48 hours later. The single-macromolecule particles had been fluorescently labelled in a similar manner to Experiments 1 and 2 with use of the particles synthesized in Experiment 4 and having a hydrodynamic diameter of 4 nm, 10 nm, 13 nm, 15 nm, or 22 nm. In particular, the single-macromolecule particles having a hydrodynamic diameter of 4 nm were evaluated as a model of an antisense therapeutic agent because the hydrodynamic diameter was equivalent to that of siRNA. Results of the experiment are shown in FIG. 5 and Table 6.

TABLE 6

Unit: dose %/g

| | Spleen | Kidney | Liver | Heart | Diaphragm | Skeletal muscle | Blood |
|---|---|---|---|---|---|---|---|
| 4 nm | 0.504 ± 0.434 | 33.947 ± 7.698 | 8.384 ± 0.987 | 0.387 ± 0.128 | 0.468 ± 0.105 | 0.290 ± 0.152 | (−0.711) ± 0.027 |
| 10 nm | 6.331 ± 1.428 | 2.062 ± 0.314 | 6.023 ± 0.841 | 1.724 ± 0.103 | 0.788 ± 0.127 | 3.249 ± 1.202 | 6.022 ± 0.841 |
| 13 nm | 8.576 ± 0.922 | 1.432 ± 0.424 | 4.423 ± 0.186 | 1.675 ± 0.286 | 0.932 ± 0.119 | 3.447 ± 1.097 | 14.540 ± 2.954 |
| 15 nm | 9.776 ± 4.879 | 1.253 ± 0.470 | 5.504 ± 0.927 | 2.316 ± 0.176 | 1.035 ± 0.189 | 2.699 ± 0.303 | 19.463 ± 0.388 |
| 22 nm | 11.966 ± 1.954 | 1.075 ± 0.093 | 4.206 ± 1.148 | 0.912 ± 0.187 | 0.663 ± 0.219 | 1.979 ± 0.144 | 17.073 ± 2.949 |

*means ± SD

As a result of the above experiments, a single macromolecule having a narrow molecular weight distribution and a controlled hydrodynamic diameter was synthesized. The narrowness of the molecular weight distribution of each PAsp-g-PEG is indicated not only by the data of molecular weight distributions but also by the fact that single peaks are obtained in the results of GPC indicated in FIG. 2.

4. Experiment 4: Evaluation of Retention in Blood

A single macromolecule controlled to have a molecular weight of 10 k to 750 kDa was synthesized, and single-macromolecule particles each consisting of the synthesized single macromolecule were used to evaluate retention in blood.

In accordance with a procedure similar to that of Experiments 1 to 3 described above, poly-L-aspartic acid was synthesized, and a given number of PEG chains each having a molecular weight of 2000 were bonded to the poly-L-aspartic acid to synthesize a single macromolecule. The molecular weight was controlled in accordance with the number of PEG chains to be bonded. A hydrodynamic diameter was evaluated, and retention in blood was evaluated with use of fluorescently-labelled macromolecules.

As indicated in FIG. 5 and Table 6, the macromolecules of a size (hydrodynamic diameter) equivalent to that of an antisense therapeutic agent were accumulated in a large amount in the kidney, which was located upstream of renal excretion, whereas the macromolecules of a size of not less than 10 nm exhibited significantly less accumulation in the kidney. Further, the macromolecules of not less than 10 nm in size exhibited an increased amount of accumulation in targeted muscular tissue, and was thus confirmed to be effective as a macromolecule conjugate.

Figure 6:
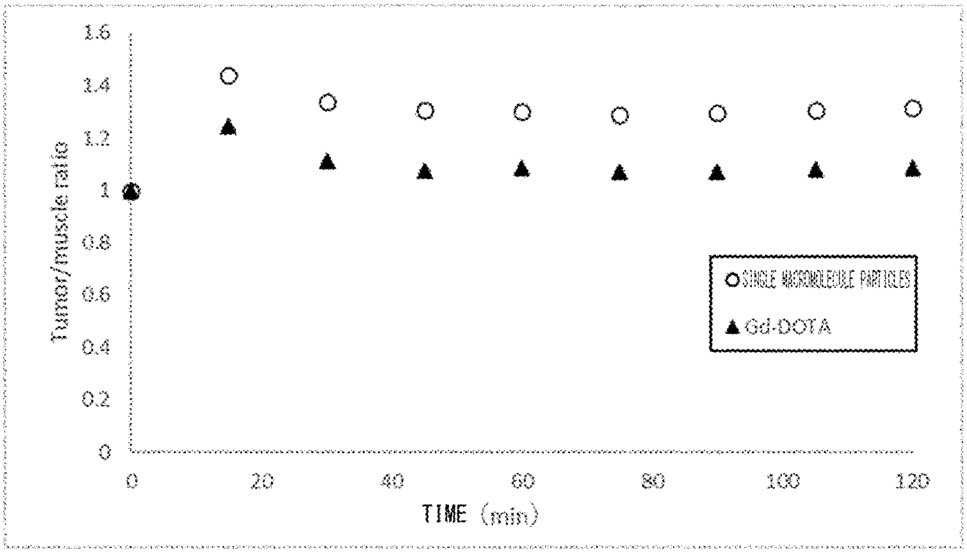
FIG. 6 indicates a result of measurement of a relaxivity of a contrast agent bonded to single-macromolecule particles in accordance with an embodiment of the present invention and a relaxivity of a conventional contrast agent.

6. Experiment 6: Evaluation of Contrast Effect on Cancer in Model Mouse Subcutaneously-Implanted with Colorectal Cancer A DOTA complex was bonded to the single macromolecule synthesized in Experiment 4 and having a hydrodynamic diameter of 12 nm to thereby cause the single macromolecule to carry Gd. A relaxivity at 0.47 T was evaluated and compared with that of Magnescope (Gd-DOTA), which is a clinically-used Gd contrast agent. The contrast agents were each intravenously administered to a model mouse subcutaneously-implanted with colorectal cancer, and a contrast effect on the cancer was evaluated using 1T-MRI. Results of the experiment are shown in Table 7 and FIGS. 7 and 8. Further, FIG. 6 indicates results of examining a ratio of a contrast effect of each contrast agent on cancer to a contrast effect of the contrast agent on muscle (a tumor/muscle ratio).

TABLE 7

| | $r_1(mM^{-1} \cdot sec^{-1})$ | $r_2(mM^{-1} \cdot sec^{-1})$ | $r_1/r_2$ |
|---|---|---|---|
| Magnescope | 3.72 | 4.68 | 0.795 |
| Single-macromolecule contrast agent | 9.56 | 10.5 | 0.903 |

Figure 7:
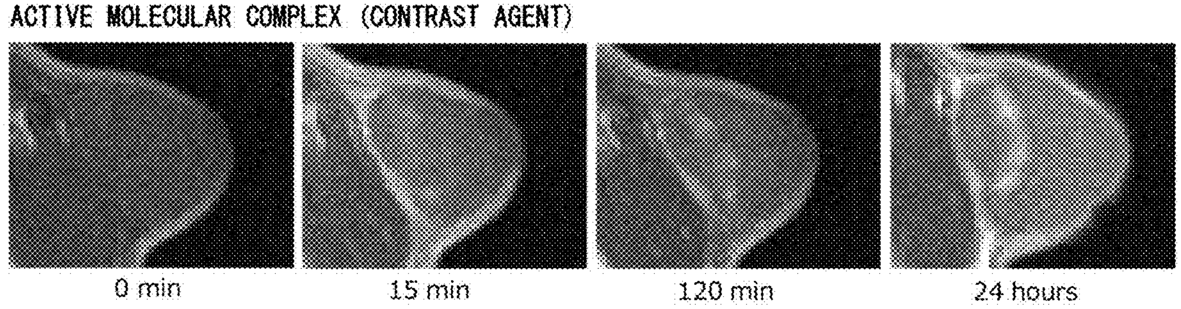
FIG. 7 indicates images captured by an active molecular complex (contrast agent) in accordance with an embodiment of the present invention.
Figure 8:
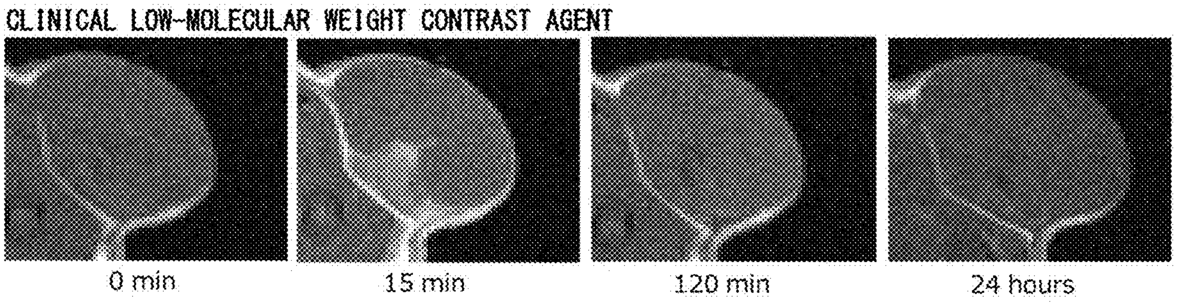
FIG. 8 indicates images captured by a conventional contrast agent.

As indicated by the results of measurement of relaxivity shown in Table 7, a relaxivity ($r_1$) and a positive effect ($r_1/r_2$) higher than those of Magnescope were obtained. Regarding a contrast effect on cancer, as shown in FIGS. 7 and 8, a contrast effect of the conventional Magnescope was very limited, whereas the single-macromolecule contrast agent exhibited an increased contrast intensity on cancer and achieved enhancement of the contrast of the entire cancer. Further, 24 hours after the contrast imaging with use of the single-macromolecule contrast agent, an even higher contrast effect (a tumor/muscle ratio of approximately 1.5) was observed.

7. Experiment 7: Evaluation of Number of Side Chains Introduced, Molecular Weight of Macromolecule Particles, and Contrast Effect In conformity to Experiment 2, PEG2000 was caused to react with a PAsp main chain at differing concentrations to synthesize five types of macromolecules having 2 to 18 PEG side chains introduced thereto. In conformity with Experiment 3, a molecular weight was measured.

Subsequently, a DOTA complex was added to these types of macromolecules to thereby cause the macromolecules to carry Gd. Similarly as in Experiment 6, a relaxivity at 0.47 T was evaluated and compared with that of Magnescope (Gd-DOTA), which is a clinically-used Gd contrast agent. Results are shown in Table 8.

TABLE 8

| | Molecular weight | Number of PEG chains introduced | Number of DOTA complexes introduced | Relaxivity | | Positive effect |
|---|---|---|---|---|---|---|
| Sample | (kDa) | Asp-g-PEG | Asp-g-DOTA | $r_1$ $(mM^{-1} \cdot sec^{-1})$ | $r_2$ $(mM^{-1} \cdot sec^{-1})$ | $r_1/r_2$ |
| Graft A | 28.7 | 2 | 19 | 26 | 27 | 0.96 |
| Graft B | 36.1 | 5 | 21 | 26.2 | 27.1 | 0.97 |
| Graft C | 34.4 | 7 | 12 | 31.8 | 32.9 | 0.97 |
| Graft D | 43.2 | 10 | 16 | 25.6 | 28.7 | 0.89 |
| Graft E | 66.1 | 18 | 26 | 21.9 | 23.6 | 0.93 |
| Magnescope | | | | 3.72 | 4.68 | 0.8 |

As indicated by the results of measurement of relaxivity shown in Table 8, appropriately selecting a side chain, the number of side chains introduced, and a molecular weight made it possible to exhibit a relaxivity considerably higher (5.9 times to 8.5 times) than that of Magnescope, which is currently clinically used, and an unprecedentedly extremely high positive effect ($r_1/r_2$) of 0.97. Such appropriate molecular design makes it possible to achieve a higher contrast in contrast imaging and to achieve a contrast of approximately the same level even in a case where the contrast agent is administered in a smaller amount.

8. Experiment 8: Acquisition of High-Precision MRI Image of Fine Structure of Cancer With use of the single-macromolecule particles having a hydrodynamic diameter of 12 nm and carrying a Gd complex used in Experiment 6, a contrast effect on cancer was evaluated in a patient-derived tumor (PDX) model (a model mouse subcutaneously-implanted with colorectal cancer).

In the experiment, the single-macromolecule particles were intravenously administered to the model mouse subcutaneously-implanted with PDS colorectal cancer, and a contrast effect on the cancer was evaluated 24 hours later.

Figure 9:
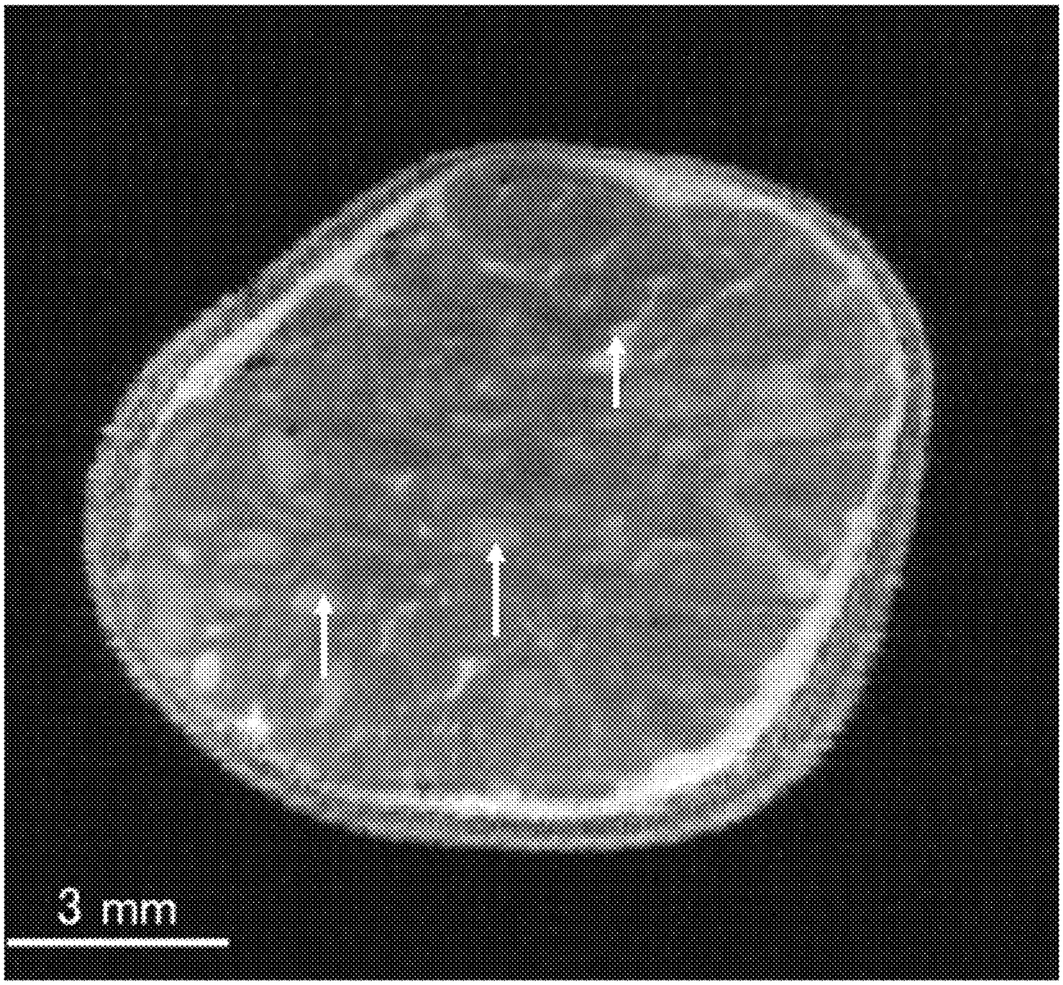
FIG. 9 indicates an image captured using a contrast agent bonded to single-macromolecule particles in accordance with an embodiment of the present invention.

As shown in FIG. 9, in MRI imaging with use of a contrast agent to which the single-macromolecule particles having a hydrodynamic diameter of 12 nm were bonded, there were a part where the contrast agent was present in a large amount and a part where the contrast agent was absent. This indicates that there were a part that could be entered by the single-macromolecule particles having a hydrodynamic diameter of 12 nm and a part that could not be entered by the single-macromolecule particles having a hydrodynamic diameter of 12 nm. This is considered to reflect a fine structure of the cancer. High signal parts (white parts) where the contrast agent were present in a particularly large amount are indicated by arrows.

The above result suggests that by changing the size of the macromolecule contrast agent, it is possible to utilize the changes as a ruler to measure the fine structure (gaps between cancer tissues). This suggests that it is possible to use nanomedicines of different sizes depending on the measured fine structure.

It is suggested that the technology of the single-macromolecule particles in accordance with an embodiment of the present invention makes it possible to select a nanomedicine of a size optimum for each cancer.

INDUSTRIAL APPLICABILITY

A composition in accordance with an embodiment of the present invention makes it possible to provide single-macromolecule particles each having a more accurately controlled hydrodynamic diameter, an active molecular complex, a method for producing the single-macromolecule particles, and a method for imaging biological tissue.

The invention claimed is:

1. Single-macromolecule particles, each formed of a single macromolecule, the single macromolecule having a molecular weight distribution $M_w/M_n$ of not more than 1.5, the single macromolecule being present in a form of single macromolecular chains in an aqueous solvent without inter-molecular secondary association, the single macromolecule being a structure including a hydrophilic macromolecule A, the structure being (i) a structure consisting of a single hydrophilic macromolecule A that is composed solely of a linear structure or (ii) a structure in which one or more side chains are bonded to one or more of units included in a main chain, the main chain consisting of a single hydrophilic macromolecule A that is a polymer molecule including a multiple repetition of the units, each of the one or more side chains being a hydrophilic macromolecule B, the hydrophilic macromolecule A being a polypeptide, a polysaccharide, a vinyl-based macromolecule, a polyether-based macromolecule, a polyester-based macromolecule, or a polyoxazoline, and the hydrophilic macromolecule B being polyalkylene glycol, polyvinyl alcohol, polyvinyl pyrrolidone, polyhydroxyethyl methacrylate, poly(2-methoxyethyl acrylate), a polyoxazoline, carboxymethyl cellulose, methyl cellulose, hydroxyethyl cellulose, or a carboxy vinyl polymer.

2. The single-macromolecule particles as set forth in claim 1, wherein the number of the one or more side chains each of which is the hydrophilic macromolecule B and which are bonded to the hydrophilic macromolecule A is not less than 1 and not more than 100.

3. The single-macromolecule particles as set forth in claim 1, wherein the single macromolecule has a molecular weight of not less than 10 kDa and not more than 1500 kDa.

4. The single-macromolecule particles as set forth in claim 1, wherein:

the hydrophilic macromolecule A is polyaspartic acid; and the hydrophilic macromolecule B is polyethylene glycol.

5. An active molecular complex, comprising:

the single-macromolecule particles recited in claim 1; and an active molecule bonded to the single-macromolecule particles.

6. The active molecular complex as set forth in claim 5, wherein the active molecule is an antibody drug, an antisense therapeutic agent, a low-molecular drug, a radiopharmaceutical, a contrast agent, or a chromophore.

7. A method for producing single-macromolecule particles each formed of a single macromolecule, the method comprising:

(i) synthesizing a hydrophilic macromolecule A by a ring-opening polymerization reaction using an $\alpha$-amino acid-N-carboxy anhydride as a raw material, the hydrophilic macromolecule A being linear; and (ii) bonding a hydrophilic macromolecule B to a reactive site of the hydrophilic macromolecule A, the single macromolecule being present in a form of single macromolecular chains in an aqueous solvent without inter-molecular secondary association, the single macromolecule being a structure in which one or more side chains are bonded to a main chain, the main chain consisting of a single hydrophilic macromolecule A, each of the one or more side chains being a hydrophilic macromolecule B, the hydrophilic macromolecule A being a polypeptide or a polyamino acid, and the hydrophilic macromolecule B being polyalkylene glycol, polyvinyl alcohol, polyvinyl pyrrolidone, polyhydroxyethyl methacrylate, poly(2-methoxyethyl acrylate), a polyoxazoline, carboxymethyl cellulose, methyl cellulose, hydroxyethyl cellulose, or a carboxy vinyl polymer.

8. A method for measuring a size of a tumor, the method comprising measuring the size of the tumor with use of single-macromolecule particles recited in claim 1.

9. A method for measuring a fine structure within a tumor, the method comprising measuring the fine structure within the tumor with use of single-macromolecule particles recited in claim 1.

10. A method for imaging biological tissue with use of single-macromolecule particles recited in claim 1.

11. The method as set forth in claim 10, wherein the biological tissue is a tumor.

12. A drug delivery system, transporting single-macromolecule particles recited in claim 1 to an intended location in a living body.

13. A contrast agent kit, comprising a plurality of active molecular complexes having respective different sizes, each of the plurality of active molecular complexes being recited in claim 5.

14. A method for measuring a size of a tumor, the method comprising measuring the size of the tumor with use of an active molecular complex recited in claim 5.

15. A method for measuring a fine structure within a tumor, the method comprising measuring the fine structure within the tumor with use of an active molecular complex recited in claim 5.

16. A method for imaging biological tissue with use of single-macromolecule particles recited in an active molecular complex recited in claim 5.

17. A drug delivery system, transporting an active molecular complex recited in claim 5 to an intended location in a living body.

18. The single-macromolecule particles as set forth in claim 1, wherein the hydrophilic macromolecule A and the hydrophilic macromolecule B are of different types.

19. The single-macromolecule particles as set forth in claim 1, wherein the hydrophilic macromolecule A is a polypeptide, a polysaccharide, a vinyl-based macromolecule, a polyester-based macromolecule, or a polyoxazoline.

20. The single-macromolecule particles as set forth in claim 1, wherein the hydrophilic macromolecule A is a polypeptide, or a polyamino acid.

* * * * *